United States Patent
Hagemeister et al.

(10) Patent No.: US 7,084,370 B2
(45) Date of Patent: Aug. 1, 2006

(54) METHOD FOR MAKING PRODUCTS BY FREEFORM LASER SINTERING

(75) Inventors: Frank Hagemeister, Bremen (DE); Ingo Uckelmann, Bremen (DE)

(73) Assignee: BEGO Medical AG (DE)

( * ) Notice: Subject to any disclaimer, the term of this patent is extended or adjusted under 35 U.S.C. 154(b) by 0 days.

(21) Appl. No.: 10/428,622

(22) Filed: May 2, 2003

(65) Prior Publication Data

US 2004/0031780 A1 Feb. 19, 2004

(30) Foreign Application Priority Data

May 3, 2002 (DE) .......................... 102 19 983

(51) Int. Cl.
*B23K 26/00* (2006.01)

(52) U.S. Cl. .................. 219/121.85; 219/121.64; 219/121.66

(58) Field of Classification Search ............ 219/121.85, 219/121.63, 121.64, 121.65, 121.66
See application file for complete search history.

(56) References Cited

U.S. PATENT DOCUMENTS

| | | | |
|---|---|---|---|
| 4,863,538 A | 9/1989 | Deckard | |
| 5,253,177 A | 10/1993 | Saito et al. | |
| 5,637,175 A | 6/1997 | Feygin et al. | |
| 5,897,825 A | 4/1999 | Fruth et al. | |
| 5,932,059 A | 8/1999 | Langer et al. | |
| 6,021,358 A | 2/2000 | Sachs | |
| 6,193,923 B1 * | 2/2001 | Leyden et al. | 264/401 |
| 2001/0035597 A1 | 11/2001 | Grigg et al. | |

FOREIGN PATENT DOCUMENTS

| | | |
|---|---|---|
| CA | 2407073 | 11/2001 |
| DE | 43 26 986 | 8/1993 |
| DE | 44 36 695 | 10/1994 |
| DE | 195 07 881 | 3/1995 |
| DE | 195 38 257 A1 | 4/1996 |
| DE | 199 48 591 | 10/1999 |
| DE | 199 52 998 A1 | 5/2001 |
| EP | 0 338 751 | 4/1989 |
| EP | 0 633 317 A1 | 5/1995 |
| EP | 655317 A1 * | 5/1995 |
| EP | 0 686 480 A2 | 12/1995 |
| EP | 0 734 842 | 3/1996 |
| EP | 1 021 997 A3 | 7/2000 |
| EP | 1 120 228 A2 | 8/2001 |
| FR | 71.471333 | 8/1973 |
| JP | 61114818 A | 6/1986 |
| WO | 97/14549 | 7/1996 |

OTHER PUBLICATIONS

Search report for 03009491.6–1253, related matter.
Search report for 03008601.1–1253, related matter.
E. Beyer, K. Wissenbach: Oberflachenbehandlung mit Laserstrahlung, Laser in Technik und Forschung, Springer Verlag 1998, ISBN 3–540–63224–7.
Fraunhofer Magazin Apr. 2002, S. 32, 33 "Schneller Zahn aus Titan".
Gastrow, Der Spritzgiesswerkzeugbau, $5^{th}$ edition, publisher: Karl Hanser Verlag Munich–Vienna, 1998, pp. 2 and 3.
Agenda EOS International User Meeting, Apr. 23/24, 2002 and layers.

* cited by examiner

*Primary Examiner*—M. Alexandra Elve
(74) *Attorney, Agent, or Firm*—Altera Law Group, LLC

(57) ABSTRACT

A method for making metallic or non-metallic products by freeform laser sintering, in which the products are fabricated from powdery material on a substrate plate in vertically additive, layer-by-layer fashion by means of a computer-controlled laser beam, characterized in that at least one support is fabricated between the substrate plate and the outer surface of the product, said support being connected via a predetermined breaking area with the outer surface of the product, wherein the predetermined breaking area is formed by reducing the strength of the support along the outer contour of the product.

10 Claims, 2 Drawing Sheets

METHOD FOR MAKING PRODUCTS BY FREEFORM LASER SINTERING

This application is claiming priority from German application, Ser. No. 102 19 983.3-24 filed on May 3, 2002.9

The invention relates to a method for making metallic or non-metallic (i.e. ceramic or plastic) products by freeform laser sintering, in which the products are fabricated from powdery material on a substrate plate in vertically additive, layer-by-layer fashion by means of a computer-controlled laser beam.

Such a method is known from U.S. Pat. No. 4,863,538, for example. When applying said method to the fabrication of products with small dimensions, such as those needed in dental technology in the form of tooth replacements and auxiliary dental parts, difficulties arise from the fact that these small products—of which several are usually built up on a substrate plate of the usual size—must resist the substantial horizontal forces relative to their inherent moment of resistance when the excess powder is stripped off during application of the next powder layer, on the one hand, and, on the other hand, must be and remain joined to the substrate plate in such a way that they can be removed from same without damage after the fabrication procedure has been completed.

The invention solves this problem by constructing at least one support between the substrate plate and the outer surface of the product, said support being joined via a predetermined breaking area with the outer surface of the product, wherein the predetermined breaking area is formed by reducing the strength of the support along the outer contour of the product. The support constitutes a sufficiently secure and stable connection between the substrate plate and the product, yet the predetermined breaking area ensures that a finished product requiring little or no follow-up work can be removed. The preferred way of reducing the strength of the support is to decrease its cross-sectional thickness and/or to provide holes through the support.

It is also advantageous to configure the support or supports with a small cross-sectional thickness and oblong shape, and to orient it/them lengthwise on the substrate plate in the direction that the powder layers are added. In this way, they provide sufficient opposition to the forces occurring on the addition of layers, but on completion of the fabrication process vertical thereto can be easily broken off from the product if they have adhered to the latter on removal from the substrate plate.

Insofar as the products to be fabricated are bowl-shaped dental products, such as caps, crowns and the like, a development of the invention provides for the latter to be built up with their full cross-section resting on the support(s). In other words, the entire base surface of the product is made first, onto which the closed, ring-shaped wall is added.

Additional advantageous developments of the invention derive from the following description of an embodiment and from the further subclaims.

Figure 1:
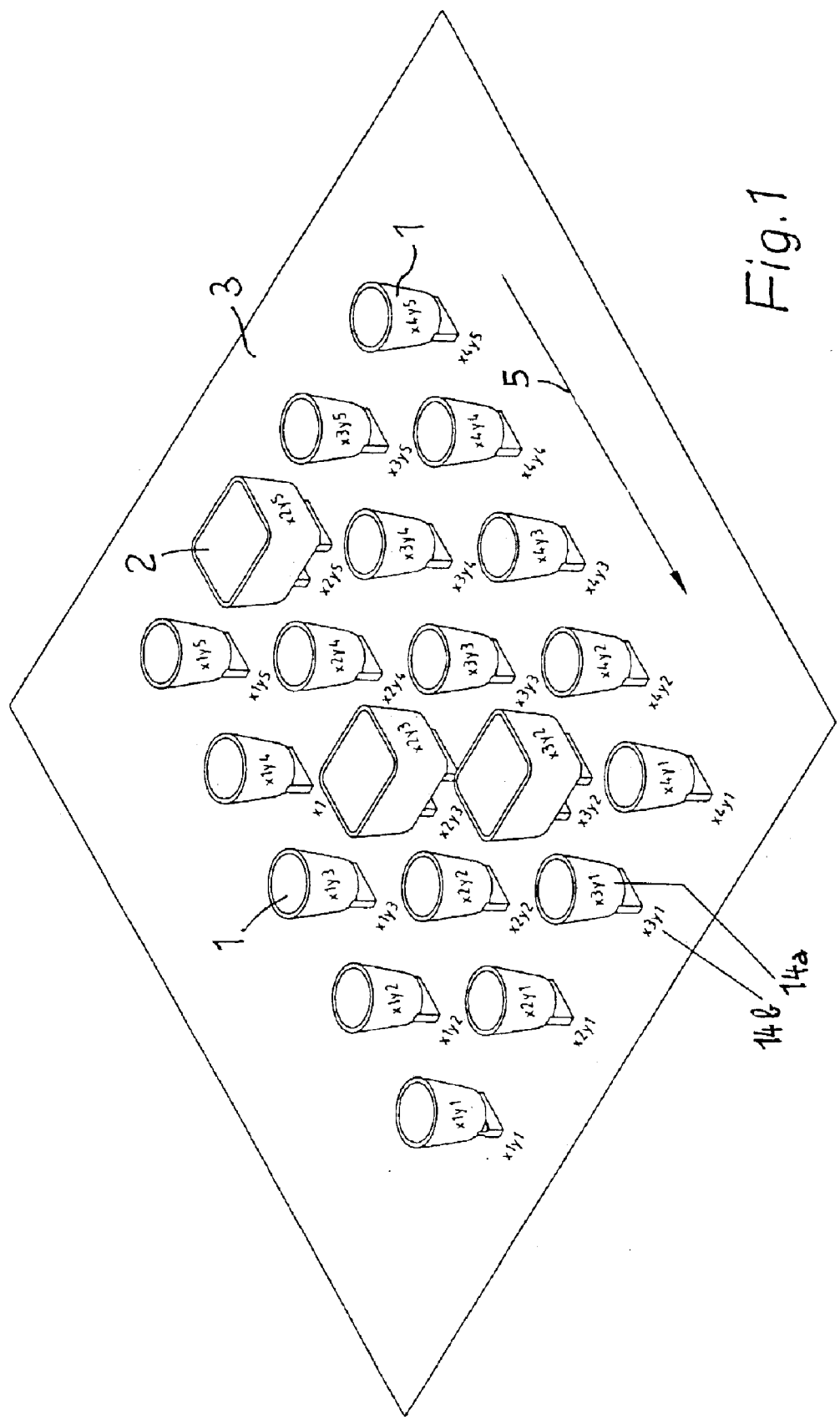
Figure 2:
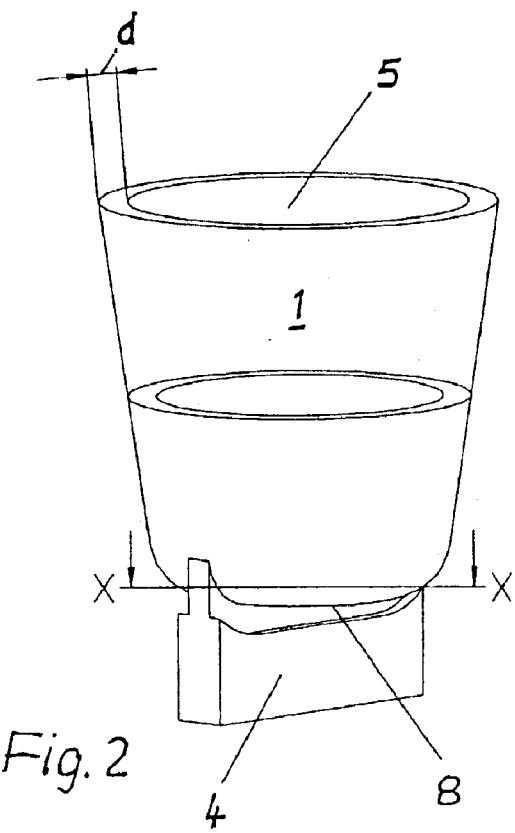
Figure 3:
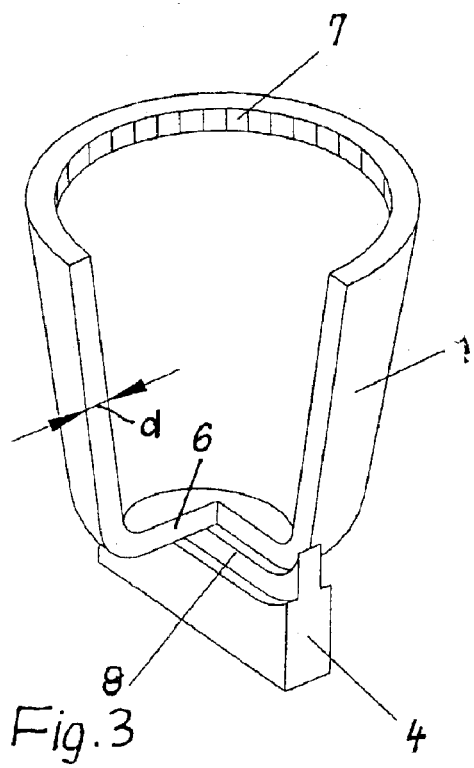
Figure 4:
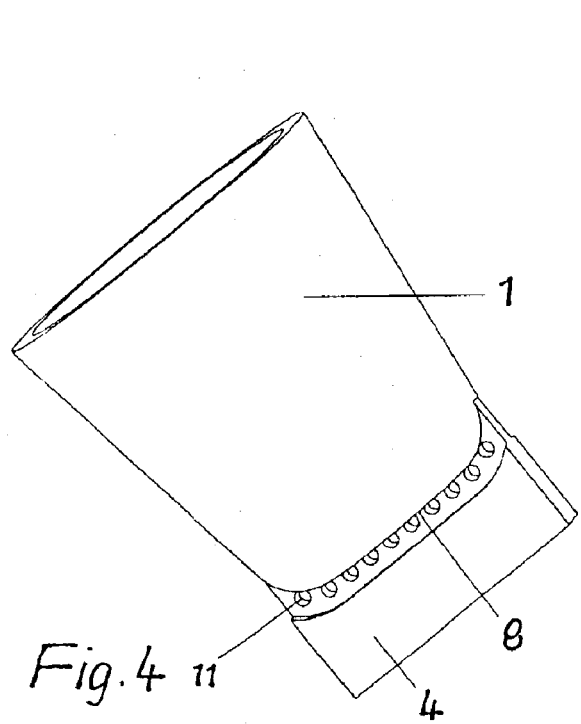
Figure 5:
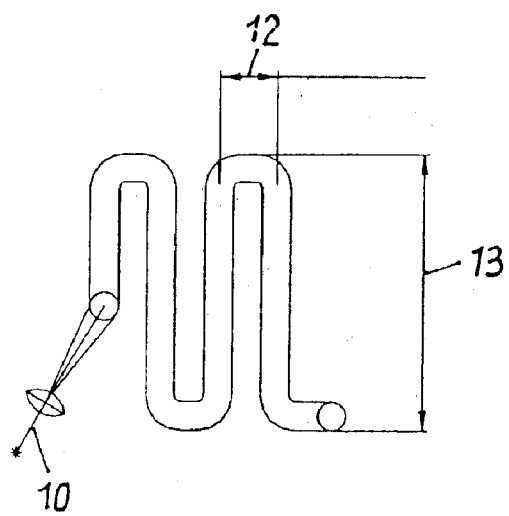

The drawings show:

FIG. 1 the arrangement and configuration, in perspective and schematic view, of a plurality of finished, bowl-shaped dental products that are still located on the substrate plate of a laser sintering apparatus;

FIG. 2 a single laser-sintered dental product with the support still attached thereto, similarly in a perspective and schematic view;

FIG. 3 the product shown in FIG. 2, in partly cutaway view;

FIG. 4 a slanted perspective view of a dental product pursuant to FIG. 2, with modified support; and FIG. 5 a greatly enlarged, schematic view of the plane laser beam track.

With the help of the notorious laser sintering method, the bowl-shaped dental products 1 and 2 shown in FIG. 1 are built up layer by layer from pulverised material, in particular metal powder of varying particle size, on a substrate plate 3 of the apparatus executing said method. Whereas the schematic view shows identically shaped bodies, in practice the latter are individually shaped, namely with the help of data, scanned intra-orally or extra-orally, about the patient's teeth or tooth stumps for which the products are intended.

FIG. 1 also shows that the separate products 1, 2 are joined to the substrate plate 3 by a support 4 (or two thereof). The supports 4 are oblong in shape and disposed lengthwise in the direction in which the powder layers are added (arrow 5), and transversely thereto are of relatively small thickness. Both aspects can be seen more precisely in FIGS. 2 and 3, which show a dental product 1 in even greater enlargement than in FIG. 1. The particle size of the respectively deposited layer may be modified—while retaining the same thickness of layer—based on the height that the product has reached.

FIGS. 2 and 3 clearly show the bowl shape of the dental product 1. In the schematic view, the thickness d of the conically annular side wall 5 is uniform over its entire height, and is equal to the thickness of the base 6; in practice, this is not the case. In particular, the edge region 7 runs to a wall thickness of 50–200 µm, but on the inner side—as suggested by FIG. 3—a thickening is performed on the inner edge region 7 by modifying the product data relative to the scanned data. In that region, the surface is smoothed by melting the surface, resulting in the inner edge surface being polished.

As also shown by FIGS. 2 and 3, the supports 4 are drawn upwards a little at their two ends, congruent with the outer surface of the product 1. Over the entire length that the support 4 is joined to the product 1, the cross-sectional thickness of the support 4 is decreased in a small part of its height—immediately adjacent to where it is joined to the outer surface of the product 1—, such that a predetermined breaking line 8 results between the outer surface of the product 1 and the support 4. By exerting lateral pressure on the product 1 against support 4, or vice versa, the support 4 can be easily and cleanly broken off from product 1. In the embodiment pursuant to FIG. 4, the predetermined breaking area or line 8 is formed by providing holes 11 in the support in addition to reducing the cross-sectional thickness of the support 4, said holes being contiguous with the outer surface of the product 1 and not only facilitating the separation of the support from the product, but also achieving a cleaner outer surface of the product. 'Holes' or 'perforations' are also understood to mean a porosity—invisible or barely visible from the outside—of the powder layer portions adjoining the outer surface of the product.

FIG. 5 shows in schematic form the path that the laser beam 10 traces when treating sufficiently large surfaces of the respective powder layer, such as the cross-sectional surface of the base 6 of a product 1 (FIG. 3). There, too, however, the edge (here annular in shape) is heated by a laser beam that is correspondingly guided in circles, and the same applies for the cross-section of thin walls. Depending on the energy input required, the track pitch 12 or the stripe width 13 is changed in the case of plane heating, and preferably according to the respective ratio of the surface—such as the surface of the base 6 of a product 1—to the length of the edge of the powder layer to be treated—such as the length of the edge of the base 6. The energy input can also be modified by changing the lumination or spot velocity of the laser beam 10, in particular by automatic means following analysis of the relevant data for the respective powder layer to be sintered. Other variables influencing the energy input are the diameter and the power of the laser beam 10. When these are modified in accordance with the surface to be sintered, the beam power is changed first and then, if necessary and permissible, the diameter of the laser beam is changed.

FIG. 1 shows two alternatives for marking the single products in a way that avoids confusion. In one case, the marking 14a is applied directly to the product, in the other case, the marking 14b is applied to the substrate plate 3 beside the product 1, in either case with laser sintered powder.

What is claimed is:

1. A method for making metallic or non-metallic products by freeform laser sintering, in which the products are fabricated from powdery material on a substrate plate in vertically additive, layer-by-layer fashion by means of a computer-controlled laser beam, wherein at least one support is fabricated between the substrate plate and the outer surface of the product, said support being connected via a predetermined breaking area with the outer surface of the product, wherein the predetermined breaking area is formed by reducing the strength of the support along the outer contour of the product, wherein holes are provided in the support in order to reduce its strength.

2. Method according to claim 1, wherein the support(s) is/are configured with small cross-sectional thickness and oblong shape, and is/are oriented lengthwise on the substrate plate in the direction that the powder layers are added.

3. Method according to claim 1, wherein bowl-shaped dental products (caps, crowns, etc.) are built up with their full cross-section resting on the support(s).

4. Method according to claim 3, wherein the wall thickness of the products is about 50–200 µm at the edge and that the product data are modified to thicken the wall accordingly.

5. Method according to claim 4, wherein the product data are modified with respect to the inside of the product.

6. Method especially (but not necessarily) according to claim 5, wherein the inner edge region is melted at the surface, i.e. to a small depth only, and in this manner smoothed ('polished').

7. Method especially (but not necessarily) according to claim 1, wherein boundary conditions of the sintering process, namely the rumination of the laser beam and/or its spot velocity and/or the track pitch and/or the stripe width (perpendicular to the track direction) are automatically changed in response to the respective ratio of the surface to the length of the edge of a sintered layer.

8. Method according to claim 7, wherein the rumination is changed primarily by changing the beam power and secondarily by changing the beam diameter.

9. Method according to claim 8, wherefore equal layer thickness, the grain size of the powder material is modified based on the height of the product that has been built up.

10. Method according to claim 9, wherein each product fabricated on the substrate plate, or the substrate plate itself in the immediate vicinity of each product, is marked by the laser beam with an identification mark.

\* \* \* \* \*

UNITED STATES PATENT AND TRADEMARK OFFICE
CERTIFICATE OF CORRECTION

| | |
|---|---|
| PATENT NO. | : 7,084,370 B2 |
| APPLICATION NO. | : 10/428622 |
| DATED | : August 1, 2006 |
| INVENTOR(S) | : Frank Hagemeister et al. |

It is certified that error appears in the above-identified patent and that said Letters Patent is hereby corrected as shown below:

On Title Page, in the field (73) Assignee:, please replace "BEGO Medical AG" with -- BEGO Medical GmbH --.

On Title Page, in the field (30) Foreign Application Priority Data, please replace "102 19 983" with -- 102 19 983.3-24 --.

Column 1, line 5, at the end of the sentence after the date listed as May 3, 2002 delete the number "9" after the period.

Signed and Sealed this

Sixteenth Day of January, 2007

JON W. DUDAS
*Director of the United States Patent and Trademark Office*